United States Patent [19]

Berguer et al.

[11] Patent Number: 5,403,265
[45] Date of Patent: Apr. 4, 1995

[54] PRESSURE SOCK

[75] Inventors: Ramon Berguer, West Bloomfield; Mary Y. Sieggreen, Northville, both of Mich.

[73] Assignee: Lunax Corporation, West Bloomfield, Mich.

[21] Appl. No.: 145,104

[22] Filed: Nov. 3, 1993

[51] Int. Cl.⁶ .......................... A61H 7/00; A61H 9/00
[52] U.S. Cl. ...................... 601/151; 602/13; 602/14; 602/27; 601/148; 128/DIG. 20
[58] Field of Search .................. 602/6, 13, 14, 27, 28, 602/29; 128/64, DIG. 20; 601/151, 148

[56] References Cited

U.S. PATENT DOCUMENTS

| | | | |
|---|---|---|---|
| 4,399,815 | 8/1983 | Bachorik | 602/13 X |
| 4,483,332 | 11/1984 | Rind | 602/13 X |
| 5,156,629 | 10/1992 | Shane et al. | 128/DIG. 20 |

FOREIGN PATENT DOCUMENTS

| | | | |
|---|---|---|---|
| 1171361 | 11/1969 | United Kingdom | 128/DIG. 20 |
| 1531268 | 11/1978 | United Kingdom | 602/13 |

*Primary Examiner*—Danton D. DeMille
*Attorney, Agent, or Firm*—Barnes, Kisselle, Raisch, Choate, Whittemore & Hulbert

[57] ABSTRACT

A pressure sock for the ambulatory treatment of venous ulcers about the ankle and lower portion of the leg of a patient. The sock has a lamina provided with a network of spaced apart, interconnected chambers which can be inflated by the introduction of fluid to exert pressure on the foot and lower leg. The sock has and an inner lining of a relatively soft, non-allergenic material and a non-distensible outer jacket.

3 Claims, 2 Drawing Sheets

PRESSURE SOCK

This invention relates to a pressure sock for the ambulatory treatment of venous ulcers about the ankle and lower portion of the leg of a patient.

BACKGROUND AND SUMMARY

The purpose of this device is to provide external pressure to the leg and foot which in turn increases tissue pressure and prevents a leakage of plasma and cells from high pressure venous loops in the capillaries. It is this leakage of plasma and cells that eventually results in the breakdown of the skin coverage and in the formation of an ulcer.

The sock preferably has a non-distensible outer jacket covering a plastic lamina with an inner lining. The lamina is formed with a network of interconnected chambers which can be pressurized to provide external pressure to the leg and foot. A standard syringe may be used to force fluid under pressure into the network and inflate the chambers. With this sock in place on the foot and lower leg of the patient, inflation of the chambers results in pressurization of the foot and lower leg because the outer jacket of the pressurized sock does not distend.

The sock is a tubular member which preferably leaves the toes exposed and extends about one third of the way up the lower part of the leg. The leg portion of the sock may be formed to provide an opening facilitating the introduction of the foot. This opening may be closed in any manner as by means of hook and loop fasteners.

Preferably a pressure relief valve is set to bleed out any excess air and prevent over inflation of the chambers. A pressure of about 45 mmHg should not be exceeded to avoid cut-off of circulation to the foot.

Preferably there are minute perforations through the sock in the spaces not occupied by the network of inflatable chambers to permit aeration of the leg and foot.

One object of this invention is to provide a pressure sock having the foregoing features.

Another object is to provide a pressure sock which is of a simple, inexpensive construction, which is relatively easy to manufacture and is highly effective in the ambulatory treatment of venous ulcers about the ankle and lower leg.

Other objects, features and advantages of the invention will become more apparent as the following description proceeds, especially when considered with the accompanying drawings.

DETAILED DESCRIPTION

Figure 1:
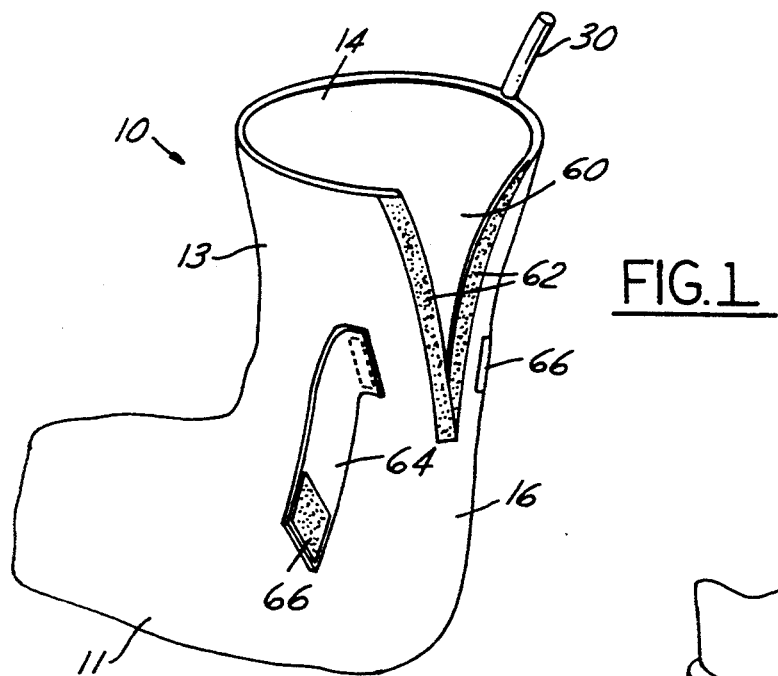
FIG. 1 is a perspective view of a pressure sock constructed in accordance with this invention, showing the opening or split at the rear which facilitates introduction of the foot.
Figure 2:
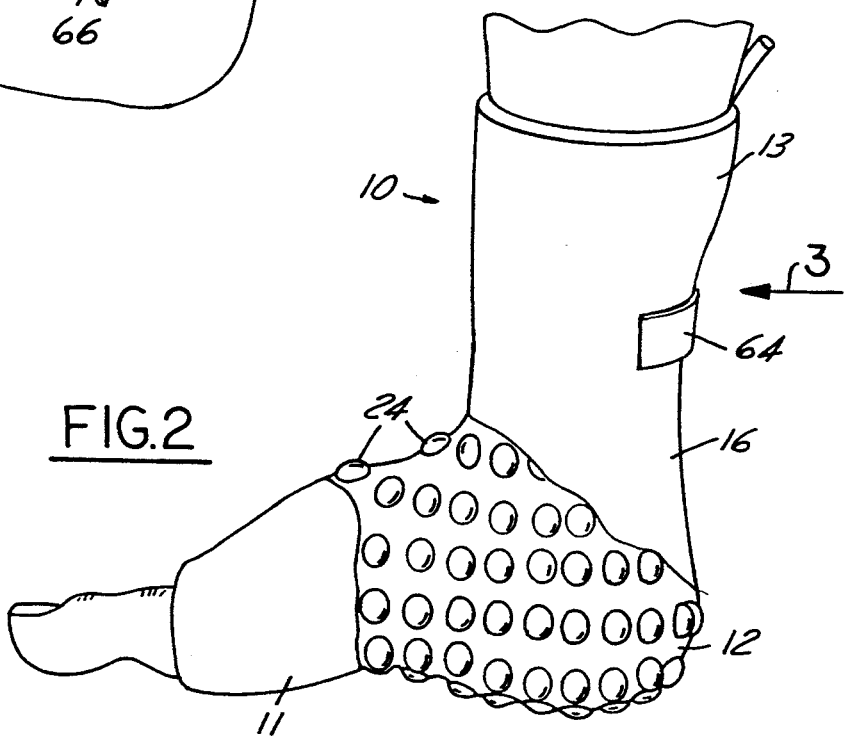
FIG. 2 is a perspective view of the sock in FIG. 1, showing the sock applied on the foot and lower leg and the network of chambers pressurized, with the outer jacket partially broken away to show the inflated chambers.
Figure 3:
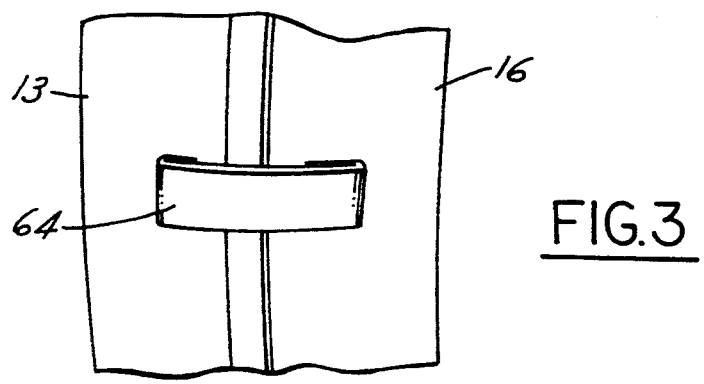
FIG. 3 is a fragmentary view taken in the direction of the arrow 3 in FIG. 2.
Figure 4:
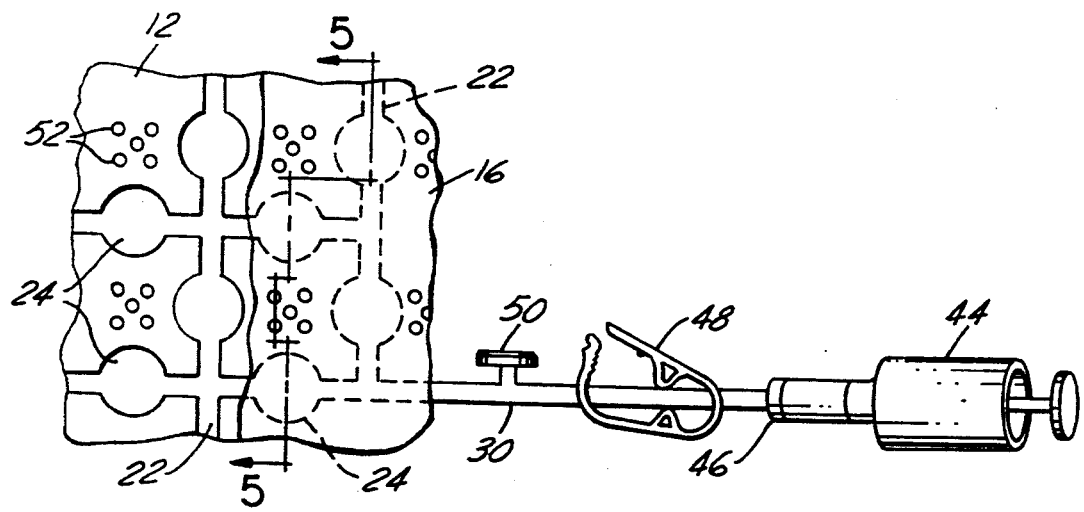
FIG. 4 is an enlarged view of a portion of the sock with part of the outer jacket broken away, showing the network of fluid chambers and connecting passages, and also showing in elevation a syringe connected to a tube for introducing air under pressure into the network of interconnected chambers.
Figure 5:
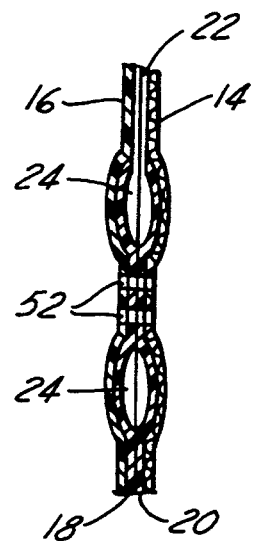
FIG. 5 is a fragmentary sectional view taken on the line 5—5 in FIG. 4.

Referring now more particularly to the drawings, the sock 10 is in the form of a tubular member which preferably is open at the bottom to leave the toes exposed and is adapted to be applied to the foot and lower third of the leg, preferably terminating below the calf. The sock 10 has a foot receiving part 11 and a contiguous leg-receiving part 13. The sock 10 comprises a flexible tubular lamina 12, an inner lining 14 and an outer cover or jacket 16 which extend throughout the full extent of the foot receiving and leg receiving parts 11 and 13.

The tubular lamina 12 may be formed of two flexible layers 18 and 20 of very thin material, preferably plastic, which is impervious to the transfer or fluid therethrough. The plastic layers may, for example, be made of polyurethane or latex and are secured together in surface-to-surface relation throughout the full extent thereof except for a network of relatively narrow passages 22 and interconnecting relative large chambers 24 which are distributed throughout the full extent of the lamina. The two layers are secured together in any suitable manner as by heat-bonding or by a suitable adhesive.

The inner lining 14 and outer jacket 16 are flexible tubular members and extend throughout the full extent of the lamina 12. The inner lining is preferably formed of a relative soft, gentle and non-allergenic material which will not irritate the skin of the foot and lower leg. Thus the inner lining may, for example, be made of paper, non-woven urethane, cotton or any natural or synthetic material which is sufficiently gentle and non-abrasive. The outer jacket is non-distensible and preferably relatively soft and non-allergenic. It may be made of a material such as polytetrafluoroethelene (TFE), Teflon or Nylon or Dacron, and is secured to the outside of the lamina 12 by any suitable means as by heat bonding or by a suitable adhesive.

A tube 30 has one end secured to the lamina 12 in communication with one of the narrow passages of the network. This tube is used to introduce fluid, such as ordinary air, into the network to inflate the chambers. The end of the tube attached to the lamina may be permanently secured in place. A syringe 44 of conventional construction may be used to pump air into the network of chambers within the lamina by attaching its outlet end to the free end of the tube. This free end of the tube may be constructed with a normally closed valve 46 which opens automatically when the syringe is applied. Alternatively, a simple clamp 48 may be provided for closing the tube and preventing air under pressure in the network within the lamina from escaping.

The tube preferably has a relief valve 50 which is normally closed but which is adapted to open when a predetermined maximum desired pressure of fluid in the network is reached. Thus the relief valve may be set to relieve pressure when the pressure reaches 45 mmHg. This will prevent over-inflation and cut-off of circulation to the foot.

Preferably minute perforations 52 through the lamina, outer jacket and inner lining, in areas not occupied by the network of narrow passages and inflatable chambers, are provided to aerate the leg and foot. If the outer jacket and inner lining are of a sufficiently porous material to allow them to breath, then the performations may be formed in the lamina only.

The syringe may be used not only for inflating the chambers of the lamina but also for deflating the chambers by aspirating with the syringe so that the sock may be removed.

Preferably the sock has a split 60 up the back and when this split is opened the sock is easily applied to and taken off the foot. This split may be closed by any suitable means as by means of strips 62 of ordinary hook and loop fasteners. A strap 64 secured at one end to the sock at one side of the split may be extended across the split and releasably secured by hook and loop fasteners 66 to the sock at the other side of the split to provide additional security of the closure. The patient may walk about with the sock inflated and in place on the foot and lower leg.

What is claimed is:

1. A pressure sock for the ambulatory treatment of venous ulcers about the ankle and lower portion of the leg of a patient, said sock having a foot-receiving part and a contiguous leg-receiving part adapted to extend along at least the lower portion of the leg, said sock having a plastic tubular lamina provided with a network comprising a multiplicity of dome-like spaced apart chambers interconnected by relatively narrow passages, a fluid inlet to said network for the introduction of fluid under pressure to inflate said chambers, a releasable valve for closing said network to retain pressure therein, an inner lining for said lamina of a relatively soft, non-allergenic material, an outer jacket for said lamina of a relatively soft, non-allergenic material, said outer jacket being non-distensible so that with the sock applied to the foot and lower portion of the leg of a patient, inflation of the chambers results in pressurization of the foot and lower portion of the leg because the outer jacket does not distend, said lamina, lining and jacket extending throughout the full extent of said foot-receiving part and said leg-receiving part and being sufficiently flexible to permit a patient to walk about with the sock applied to the foot and the lower portion of the leg and the chambers inflated.

2. A sock as defined in claim 1, and further including a plurality of perforations through said lamina, lining and jacket which do not penetrate said network of chambers and interconnecting passages, to permit aeration of the leg and the foot.

3. A sock as defined in claim 2, and further including a relief valve to bleed off any excess pressure in said network of chambers and interconnecting passages.

* * * * *